United States Patent
Link

(10) Patent No.: US 11,213,399 B2
(45) Date of Patent: Jan. 4, 2022

(54) REVISION PROSTHESIS SHAFT FOR A REVISION JOINT ENDOPROSTHESIS

(71) Applicant: Waldemar Link GmbH & Co. KG, Hamburg (DE)

(72) Inventor: Helmut D. Link, Hamburg (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 139 days.

(21) Appl. No.: 16/466,239

(22) PCT Filed: Dec. 5, 2017

(86) PCT No.: PCT/EP2017/081570
§ 371 (c)(1),
(2) Date: Jun. 3, 2019

(87) PCT Pub. No.: WO2018/104331
PCT Pub. Date: Jun. 14, 2018

(65) Prior Publication Data
US 2020/0060832 A1    Feb. 27, 2020

(30) Foreign Application Priority Data
Dec. 6, 2016 (EP) .................................... 16202345

(51) Int. Cl.
*A61F 2/36* (2006.01)
*A61F 2/30* (2006.01)

(52) U.S. Cl.
CPC ........ *A61F 2/3676* (2013.01); *A61F 2/30724* (2013.01); *A61F 2/367* (2013.01);
(Continued)

(58) Field of Classification Search
CPC .... A61F 2/3676; A61F 2/367; A61F 2/30724; A61F 2002/3674; A61F 2/3672;
(Continued)

(56) References Cited

U.S. PATENT DOCUMENTS 4,871,369 A * 10/1989 Muller ................. A61F 2/3662
                                                        623/23.35
4,895,572 A *  1/1990 Chernoff .............. A61F 2/36
                                                        623/23.27
(Continued)

FOREIGN PATENT DOCUMENTS

DE     43 20 086 A1   12/1994
DE     299 07 259 U1   9/1999
(Continued)

OTHER PUBLICATIONS

International Search Report and Written Opinion dated Apr. 9, 2018 in corresponding International Application No. PCT/EP2017/081570.
(Continued)

*Primary Examiner* — Alvin J Stewart
(74) *Attorney, Agent, or Firm* — Joseph V. Saphia; Haug Partners LLP

(57) ABSTRACT

The invention relates to a revision prosthesis shaft of a revision joint endoprosthesis for anchoring in an elongate bone (9), in particular femur. The surface is designed for adhesive agent-free fastening in the proximal epimetaphysis (91) and the diaphysis (92) of the bone. According to the invention, a distal epimetaphyseal extension (2) is provided at the far end of the shaft (12), the tip of which extension reaches into the distal epimetaphysis (93) of the bone. The extension (2) is designed for fastening in the distal epimetaphysis (93) by means of an adhesive agent (3), in particular bone cement. The invention combines the advantages of cement-free fastening, namely of the shaft in itself in the diaphysis (92), with the advantages of cemented fastening, namely of the extension in the distal epimetaphysis (93). Even in difficult cases in which sufficient hold previously could not be achieved for lack of fastening distance in the diaphysis, stable anchoring can thus be achieved. This (Continued)

increases the safety and longevity of the revision. The invention further relates to a corresponding implantation method.

17 Claims, 4 Drawing Sheets

(52) U.S. Cl.
CPC .............. *A61F 2002/3069* (2013.01); *A61F 2002/30156* (2013.01); *A61F 2002/30449* (2013.01); *A61F 2002/30606* (2013.01); *A61F 2002/3686* (2013.01)

(58) Field of Classification Search
CPC ............ A61F 2/4684; A61F 2002/3686; A61F 2002/368; A61F 2002/3698; A61F 2002/30614; A61F 2002/30616; A61F 2002/30607; A61F 2002/3069; A61F 2/3662

See application file for complete search history.

(56) References Cited

U.S. PATENT DOCUMENTS

| | | | | |
|---|---|---|---|---|
| 4,908,032 | A * | 3/1990 | Keller | A61F 2/30721 623/23.45 |
| 4,983,183 | A * | 1/1991 | Horowitz | A61B 17/8802 128/898 |
| 5,002,578 | A * | 3/1991 | Luman | A61F 2/36 623/22.42 |
| 5,032,130 | A * | 7/1991 | Schelhas | A61F 2/3672 623/22.42 |
| 5,108,405 | A * | 4/1992 | Mikhail | A61B 17/175 606/80 |
| 5,108,452 | A * | 4/1992 | DeMane | A61F 2/30734 623/22.42 |
| 5,181,928 | A * | 1/1993 | Bolesky | A61F 2/36 623/22.42 |
| 5,219,363 | A * | 6/1993 | Crowninshield | A61F 2/30907 623/23.34 |
| 5,489,309 | A * | 2/1996 | Lackey | A61F 2/40 623/19.14 |
| 5,507,817 | A * | 4/1996 | Craig | A61F 2/4059 623/20.11 |
| 5,645,601 | A * | 7/1997 | Pope | A61F 2/30767 623/23.39 |
| 5,658,349 | A * | 8/1997 | Brooks | A61F 2/30739 623/23.23 |
| 5,725,595 | A * | 3/1998 | Gustilo | A61F 2/30767 623/23.15 |
| 5,961,555 | A * | 10/1999 | Huebner | A61F 2/40 623/19.11 |
| 5,976,188 | A * | 11/1999 | Dextradeur | A61B 17/8802 623/23.23 |
| 5,984,968 | A * | 11/1999 | Park | A61B 17/8802 623/16.11 |
| 6,143,030 | A * | 11/2000 | Schroder | A61F 2/4601 623/16.11 |
| 6,299,648 | B1 * | 10/2001 | Doubler | A61F 2/36 623/23.18 |
| 6,332,896 | B1 * | 12/2001 | Hubbard | A61F 2/3662 623/23.24 |
| 7,297,163 | B2 * | 11/2007 | Huebner | A61F 2/4657 623/19.11 |
| 7,481,841 | B2 * | 1/2009 | Hazebrouck | A61F 2/36 623/18.12 |
| 8,668,692 | B1 * | 3/2014 | Lindvall | A61F 2/3676 606/62 |
| 9,504,578 | B2 * | 11/2016 | Hood | A61F 2/30734 |
| 2002/0045950 | A1 * | 4/2002 | Draenert | A61F 2/36 623/23.26 |
| 2002/0177901 | A1 * | 11/2002 | Howie | A61F 2/3662 623/23.35 |
| 2003/0074078 | A1 * | 4/2003 | Doubler | A61F 2/36 623/22.42 |
| 2004/0010319 | A1 * | 1/2004 | McTighe | A61F 2/389 623/23.21 |
| 2004/0117023 | A1 * | 6/2004 | Gerbec | A61F 2/36 623/18.11 |
| 2004/0117024 | A1 * | 6/2004 | Gerbec | A61F 2/38 623/18.11 |
| 2004/0254646 | A1 * | 12/2004 | Stone | A61F 2/4059 623/23.15 |
| 2005/0125067 | A1 * | 6/2005 | Sweeney | A61F 2/4612 623/19.14 |
| 2006/0004459 | A1 * | 1/2006 | Hazebrouck | A61F 2/36 623/18.12 |
| 2006/0129247 | A1 * | 6/2006 | Brown | A61B 17/164 623/23.46 |
| 2006/0167554 | A1 * | 7/2006 | Heck | A61F 2/384 623/20.15 |
| 2006/0184250 | A1 * | 8/2006 | Bandoh | A61F 2/36 623/23.32 |
| 2007/0118229 | A1 * | 5/2007 | Bergin | A61F 2/30771 623/23.31 |
| 2008/0167723 | A1 * | 7/2008 | Acker | A61F 2/3662 623/22.4 |

FOREIGN PATENT DOCUMENTS

| | | |
|---|---|---|
| EP | 0 319 171 A1 | 6/1989 |
| EP | 0 359 485 A1 | 3/1990 |
| EP | 2 491 893 A1 | 8/2012 |
| FR | 2 674 744 A1 | 10/1992 |
| FR | 2 875 397 A1 | 3/2006 |

OTHER PUBLICATIONS

Li Jian-long, et al., "Selection of prosthesis size before total hip arthroplasty," Chinese Journal of Tissue Engineering Research, Nov. 25, 2012, vol. 16, No. 48, pp. 8943-8947.

Liu Hong-wei et al., "The measurement of proximal femoral medullary cavity and the selection of different types of femoral prosthesis," Chinese Journal of Clinical Anatomy, vol. 29, No. 1, 2011, pp. 67-71 and 76.

Office Action dated Apr. 28, 2021 issued in corresponding Chinese Patent Application No. 201780073907.2.

* cited by examiner

REVISION PROSTHESIS SHAFT FOR A REVISION JOINT ENDOPROSTHESIS

CROSS-REFERENCE TO RELATED APPLICATIONS

This application is the National Stage entry under 35 U.S.C. § 371 of International Application No. PCT/EP2017/081570 filed on Dec. 5, 2017, published on Jun. 14, 2018 under Publication Number WO 2018/104331, which claims the benefit of priority under 35 U.S.C. § 119 of European Patent Application Number 16202345.1 filed Dec. 6, 2016, the entireties of which are herein incorporated by reference.

The invention relates to a revision prosthesis shaft of a revision joint endoprosthesis for anchoring in an epimetaphyseal region of an elongate bone. The revision prosthesis shaft has, at the upper end, a neck part for receiving a joint piece and, adjoining the neck part, a shaft part whose surface is designed for adhesive agent-free (cementless) fastening in the epimetaphysis. The length of the shaft part is dimensioned such that it reaches at least into the diaphysis of the bone.

A problem that occurs in the replacement (revision) of joint endoprostheses is that the bone receiving the prosthesis is often damaged. This is due in particular to defects at the bone substance or bone surface caused by the extraction of the existing prosthesis, possibly aggravated by further defects on the bone. However, in order also to achieve sufficiently secure anchoring of the replacement joint endoprosthesis, the shafts of the revision prostheses are made particularly long (long shaft). The shaft is dimensioned such that it protrudes into a deeper region with load-bearing bone substance (diaphysis). The diaphysis is the narrow, mostly cylindrical central region of an elongate tubular bone, for example of the femur.

Revision prosthesis systems with such a revision shaft are known inter alia as the MP reconstruction prosthesis system from Waldemar Link GmbH & Co. KG, Hamburg, Germany. In this system, the shaft is designed such that it can be implanted free of cement in its upper (proximal) region. This allows the damaged bone to regenerate. The length of the shaft is dimensioned such that it reaches into the diaphysis of the femur. There, a fastening distance of 40 to 80 mm is necessary in order to achieve sufficiently secure anchoring.

It has been found in clinical practice that, in revision operations, this required fastening distance cannot always be ensured. A sufficiently stable anchoring of the revision shaft can then no longer be obtained. This can subsequently lead to a loosening of the shaft and to a reduced useful life of the revision prosthesis. This is a considerable disadvantage.

The object of the invention is therefore to make available an improved revision shaft that avoids this disadvantage.

The solution according to the invention lies in the features of the independent claims. Advantageous developments are the subject matter of the dependent claims.

In a revision prosthesis shaft of a revision joint endoprosthesis for anchoring in an epimetaphyseal region of an elongate bone, in particular femur, which comprises an epimetaphysis, a diaphysis and a distal epimetaphysis, wherein the revision prosthesis shaft has, at the upper end, a neck part for receiving a joint piece and, adjoining the neck part, a shaft part whose surface is designed for adhesive agent-free (cementless) fastening in the epimetaphysis and diaphysis and whose length is dimensioned such that it reaches into the diaphysis of the bone, provision is made according to the invention that a distal epimetaphyseal extension for the shaft is provided at the far end of the shaft part, the length of which extension is dimensioned such that its tip reaches into the distal epimetaphysis of the bone, wherein the extension is designed for fastening in the distal epimetaphysis with an adhesive agent, in particular bone cement.

A number of terms used will first of all be explained below.

A revision shaft is understood as a joint endoprosthesis shaft which serves to replace a shaft of an existing joint endoprosthesis. It is designed also to be anchored in a bone that has been damaged through extraction of the previous prosthesis and/or further defects.

The neck part is understood as a region of the joint endoprosthesis on which a joint element is arranged. For example, in the case of a femoral component of a hip prosthesis, the neck part is the upper region onto which a spherical head is mounted as joint element. Correspondingly, the shaft part is understood as the shaft region which, in the case of a femoral component, is pushed into the medullary cavity of the femur.

An adhesive agent is understood in the present case as a material that binds through adhesive action, for example bone cement (e.g. of polymethyl methacrylate).

Total shaft is understood as the totality of neck part, shaft part and extension. Total length is therefore understood as the length of the total shaft.

After the first implantation of a joint endoprosthesis, an exchange is often necessary after a certain period of time, particularly if the joint endoprosthesis is defective or worn. A problem that arises here is that the receiving bone is often damaged at its surface.

A bone for receiving the revision shaft is mostly of a tubular shape. Its end region is designated as the epimetaphysis (a contraction of epiphysis and metaphysis), and the central (often approximately cylindrical) region in the middle is designated as the diaphysis. In the present case, the epimetaphysis is the end of the bone where the revision shaft is arranged with its neck part. The shaft part extends from the epimetaphysis into the diaphysis. The region adjoining the opposite end of the diaphysis is in the present case designated as the distal epimetaphysis. "Distal" is a specialist term from anatomy and denotes the opposite of "proximal".

The core of the invention is the concept of using the extension to create a continuation of the shaft which extends beyond the diaphysis into the opposite epimetaphysis (distal epimetaphysis) in order to be anchored there. Thus, on the one hand, a remote anchoring point is utilized which, on account of lever action, permits favorable force conditions. On the other hand, use is made of a bone region which has not hitherto been used for anchoring and which is therefore not already damaged by extraction. With this combination, considerably improved and more secure anchoring is achieved by surprisingly simple means, even in difficult revision cases. The fastening is thus staggered by region from proximal to distal: region of the proximal epimetaphysis cementless, region of the diaphysis cementless, region of the distal epimetaphysis cemented, where the terms "cementless" and "cemented" respectively denote fastening without adhesive agent and fastening with adhesive agent, e.g. bone cement.

The use of the distal epimetaphysis for the anchoring had not hitherto been considered. This is because the medullary cavity widens there in relation to the narrow cross section in the diaphysis. The prosthesis shaft sits tightly in the diaphysis through close contact with the bone wall. However, the medullary cavity widens in the distal epimetaphysis, such that contact is absent there and anchoring is insufficient. The shaft guided through the diaphysis cannot find a hold there. Thus, a possibly insufficient hold of a revision shaft (e.g. caused by too short a fastening distance in the diaphysis) could not hitherto be improved.

The invention has recognized that stable and secure anchoring can be achieved through a combination of an extension reaching into the distal epimetaphysis and of the extension being fastened by means of bone cement (or another adhesive agent). The invention combines, in an original way, a shaft which is provided per se for cementless implantation and an extension which reaches into the distal epimetaphysis and is designed to be anchored with cement. It thus combines the advantages of cementless fastening of the shaft, which is important specifically for a revision shaft, and of cemented fastening in the distal epimetaphysis. It thus solves the hitherto unsolved problem of achieving improved anchoring of the shaft in order to protect against loosening. The shaft according to the invention can thus provide stable and permanent anchoring even in difficult cases where no adequate hold could hitherto be achieved on account of an insufficient fastening distance in the diaphysis. The durability of the prosthesis thus greatly increases, and the important risk of the patient suffering complications is greatly reduced.

The extension is advantageously configured as a single piece. This is understood as meaning that the extension is in one piece when viewed along its entire cross section. This avoids disadvantages that result from a composite structure (consisting of core and mantle).

In relation to the total length of the shaft, the transition between shaft region and extension preferably lies in the region of 60-75% of the total length of the shaft. It has been found that, with this dimensioning, the shaft part is arranged predominantly in the diaphysis while the extension is not (or is arranged therein only by a small amount). This is favorable as regards fixing, since the shaft part is designed for a cementless fit.

The shaft part expediently forms, with the extension, a kinked shaft. This means that the central axes of the shaft part per se and of the extension are not parallel and instead form a (small) angle, the kink angle. Preferred values for the kink angle are 1° to 5°. In the present case, the term "kink" denotes the offset of the central axes; it comprises both a sharp, narrowly localized angle transition and also a gentle arc-like profile extending over a considerable distance. This permits easier insertion of the extension with the shaft part, and it also allows the extension to be positioned favorably in the medullary cavity of the distal epimetaphysis for fastening with an adhesive agent (cement). Particularly in the case of a sharp kink, the actual kink site can lie precisely at the transition between shaft part and extension. However, this is not absolutely necessary. The kink site can also be located away from the transition, preferably close by. A configuration of the kink as a generally arc-shaped profile (without a sharply limited kink site) has proven useful. The extension itself is then preferably substantially straight in the distal region.

The extension advantageously has a tapering configuration in the region of its tip. Insertion is thus made easier, particularly through the relatively narrow diaphysis.

The extension preferably has a non-round cross section which is shaped to inhibit rotation. Protection against undesired turning in the cement is thus obtained. Here, the anchoring by means of adhesive agent (cement) permits a freer configuration of the cross section than would be possible in the case of a cementless configuration reliant on the incorporation of bone substance. Advantageous embodiments for the cross section are, for example, triangular or cross-shaped, in each case preferably with rounded corners in order to avoid cutting and stress concentrations.

The extension is preferably dimensioned according to the dimensions of the shaft part. It has proven expedient if the extension is of such a length that the total length of the shaft is at least 22 times the diameter. A favorable configuration adapted to the anatomical requirements can thus be obtained.

The shaft part is often configured in one piece with the extension. This affords the advantage of easier use and of more favorable production. However, provision can also be made that the extension is configured separately. This affords the advantage of the extension being able to be inserted independently. Particularly in the case of difficult anatomical circumstances, for example a curved diaphysis, this permits improved handling. However, according to a particularly preferred embodiment, provision can also be made that a coupling site is provided which allows insertion of the extension from the opposite side. The coupling site is preferably rotationally fixed in the coupled state. The extension can thus be first introduced from the other side (from the tibial side of the femur in the case of the femoral component of a hip prosthesis) and fixed by means of the adhesive agent (cement). Thereafter, the prosthesis shaft is inserted as usual from the proximal side and is connected to the extension. It is thus also possible to solve access problems that could otherwise be overcome only with difficulty.

A centering element for the extension is preferably provided for arrangement in the distal epimetaphysis. Alignment of the extension before the cementing is thus made easier.

The extension is expediently configured such that it has an elastic modulus of 100 to 250 GPa, preferably of 180 to 230 GPa. Good adaptation to the stiffness of the bone and the cemented anchoring can thus be achieved. A preferred material for the extension or for the entire revision shaft prosthesis is cobalt-chromium-molybdenum (CoCrMo).

The revision prosthesis shaft is expediently of a modular configuration, in particular with an exchangeable neck part. Through the use of different neck parts, this permits optimal adaptation to the particular anatomical conditions.

The invention further extends to a method for implanting said revision prosthesis shaft. In the method for implanting a revision prosthesis shaft of a revision joint endoprosthesis for anchoring in an epimetaphyseal region of an elongate bone, in particular femur, with an epimetaphysis, a diaphysis and a distal epimetaphysis, wherein the revision prosthesis shaft has, at the upper end, a neck part for receiving a joint piece and, adjoining the neck part, a shaft part whose surface is designed for adhesive agent-free (cementless) fastening in the epimetaphysis and whose length is dimensioned such that it reaches into the diaphysis of the bone, and a distal epimetaphyseal extension is provided at the far end of the shaft part, the length of which extension is dimensioned such that its tip reaches into the distal epimetaphysis of the bone, wherein the extension is designed for cemented fastening in the distal epimetaphysis, the following steps are provided according to the invention:

inserting the shaft part with the neck part from the proximal direction into the epimetaphyseal region of the elongate bone, creating a receiving bed of adhesive material in the distal epimetaphysis, inserting the extension into the distal epimetaphysis, wherein the extension forms a continuation of the shaft part beyond the diaphysis into the distal epimetaphysis.

Examples of advantageous embodiments of the invention are explained below with reference to the drawing, in which.

Figure 4:
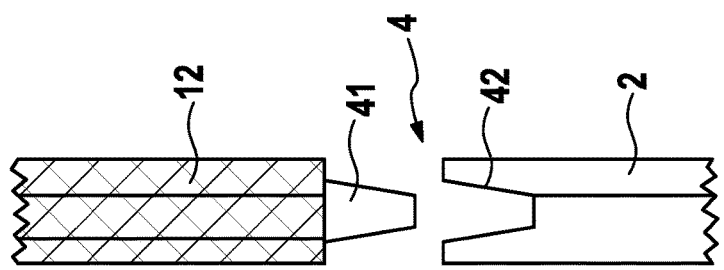
Figure 7:
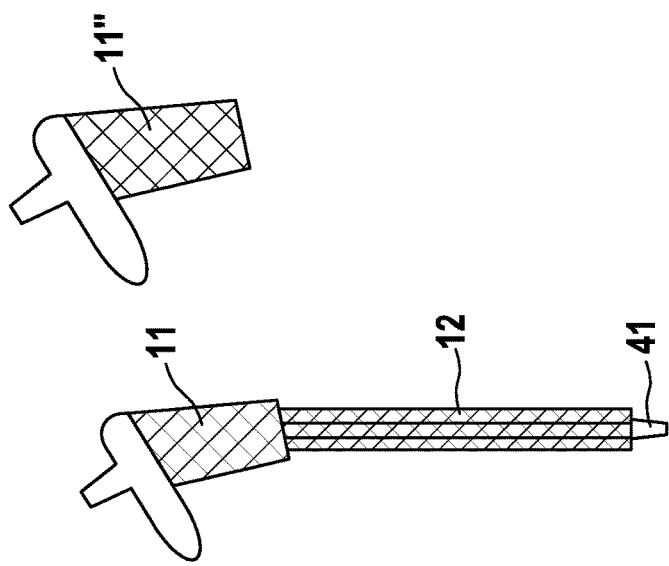
Figure 6:
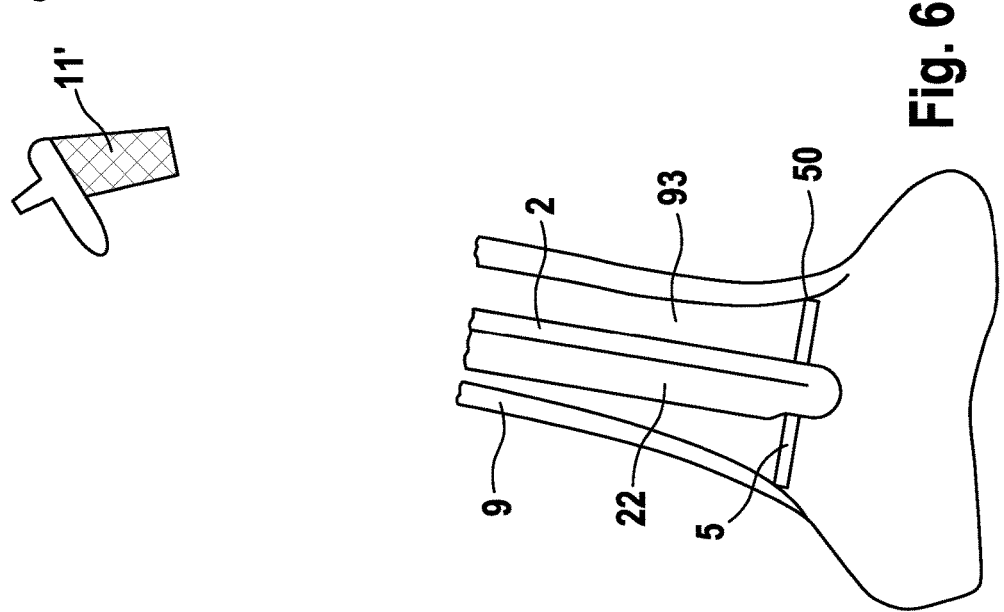
Figure 5:
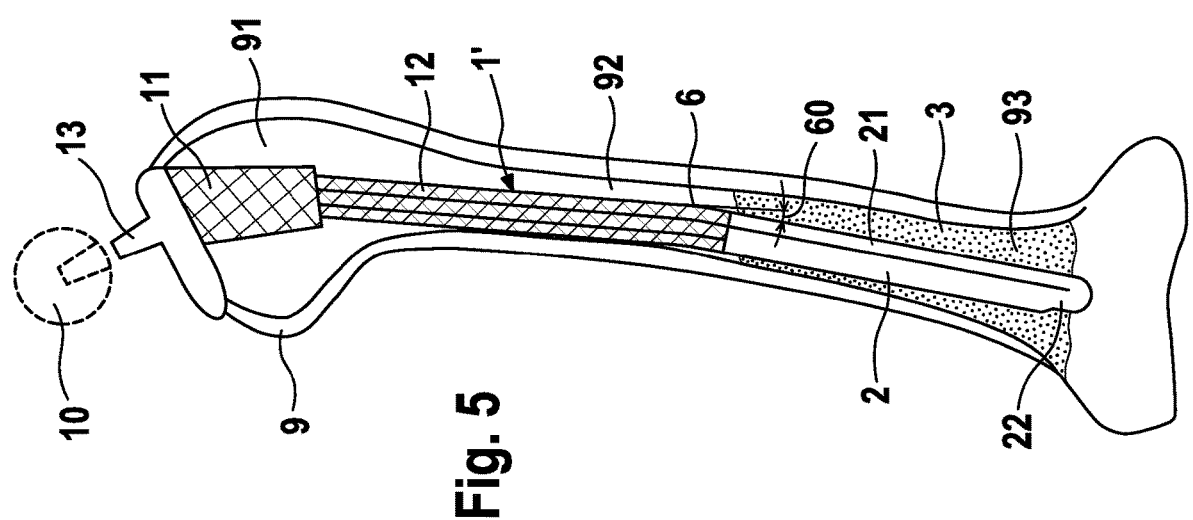
Figure 8:
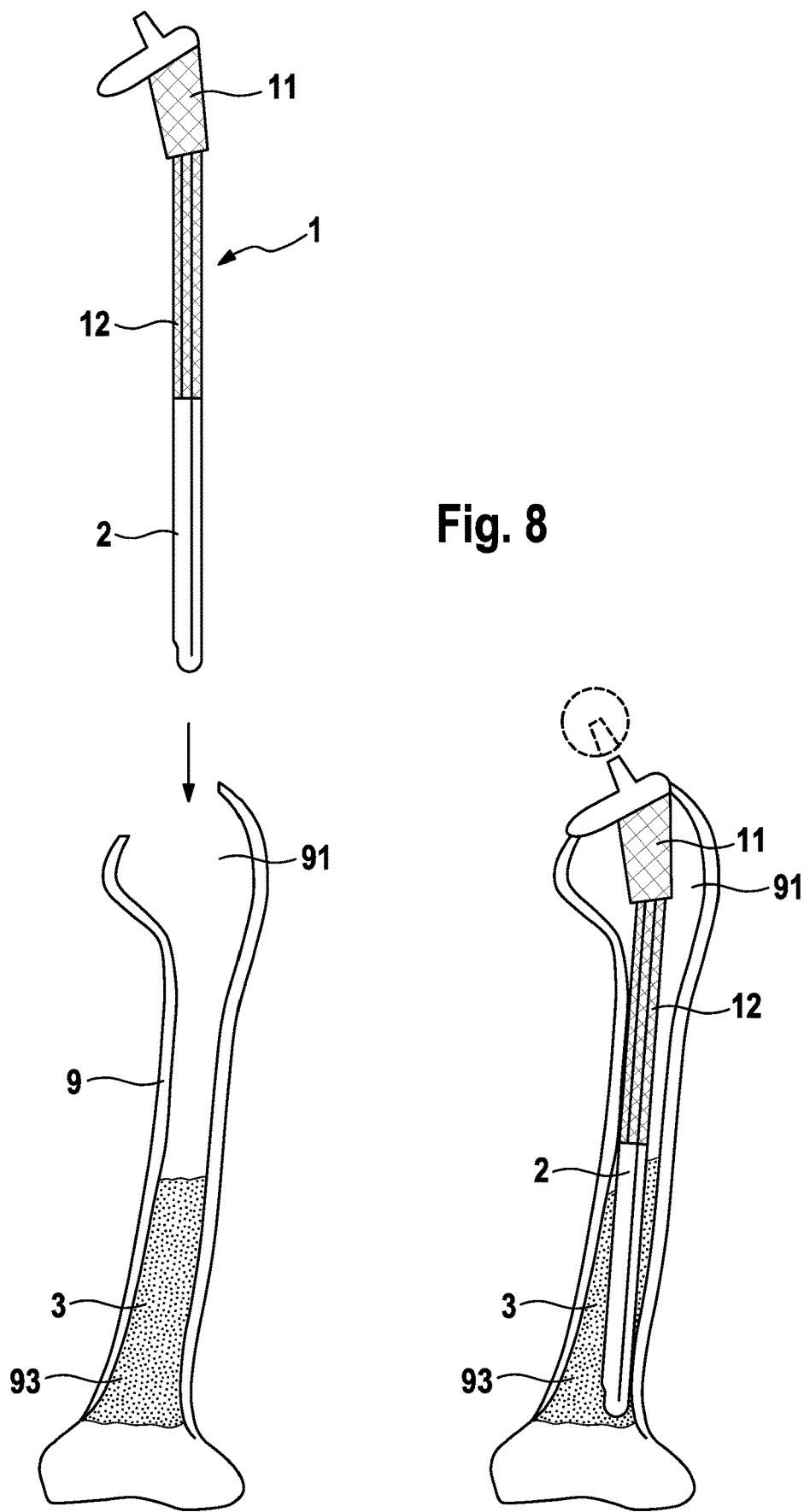

FIGS. 3a-c show alternative cross sections of the extension;

FIG. 4 shows a coupling between shaft part and extension;

FIG. 5 shows an alternative embodiment of a revision prosthesis shaft;

FIG. 6 shows a centering element on the extension;

FIG. 7 shows a prosthesis set with alternative neck parts;

FIG. 8 shows a sequence in the insertion of the revision prosthesis shaft; and

Figure 9:
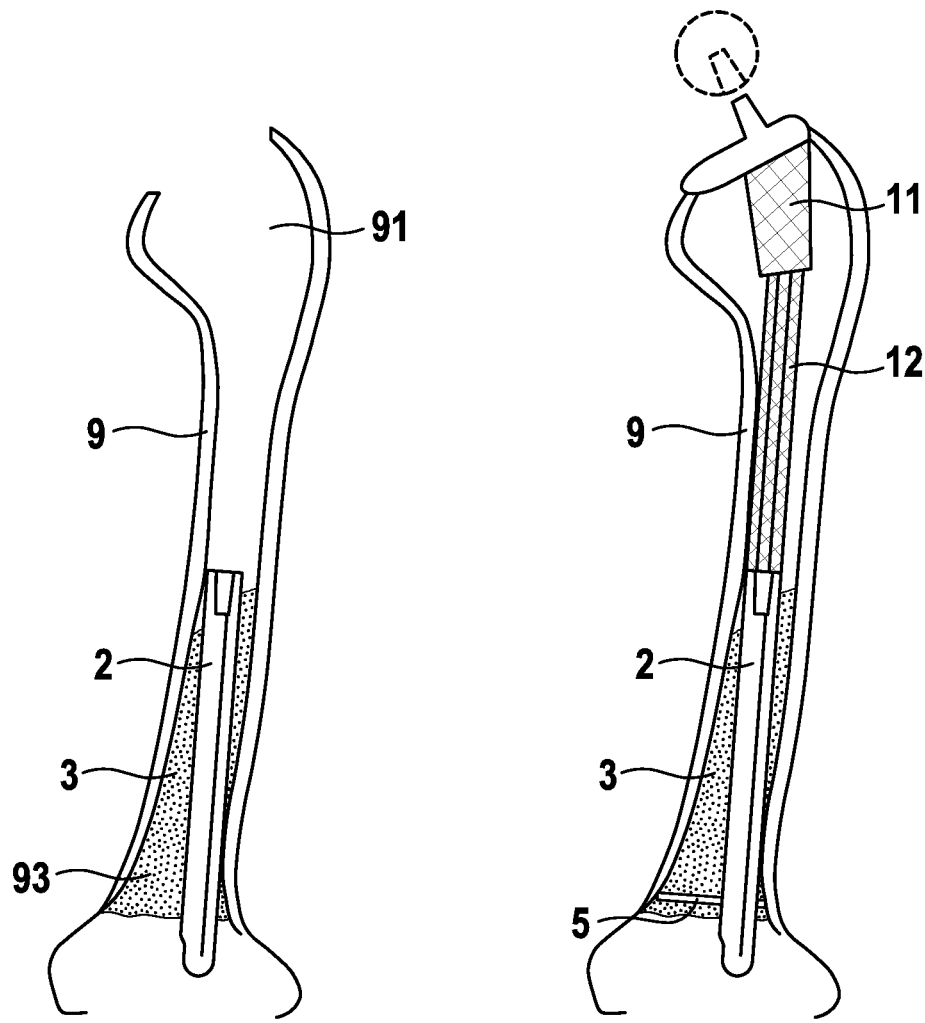

FIG. 9 shows an alternative sequence in the insertion of the revision prosthesis shaft.

The embodiment shown in the figures is a femoral component of a hip-joint endoprosthesis which, in addition to the femoral component, moreover comprises an acetabular component (not shown).

The femoral component comprises a revision shaft 1 with a neck part 11 in the upper proximal region and with a shaft part 12 in the lower distal region. It is inserted into an elongate tubular bone, which in the present case is a femur 9. At its upper end directed toward the acetabulum (not shown), the latter has an epimetaphysis 91, in its middle region it has a diaphysis 92, and, in its lower region directed toward the tibia (not shown), it has a further epimetaphysis, which in the present case is designated as the distal epimetaphysis 93.

Figure 1:
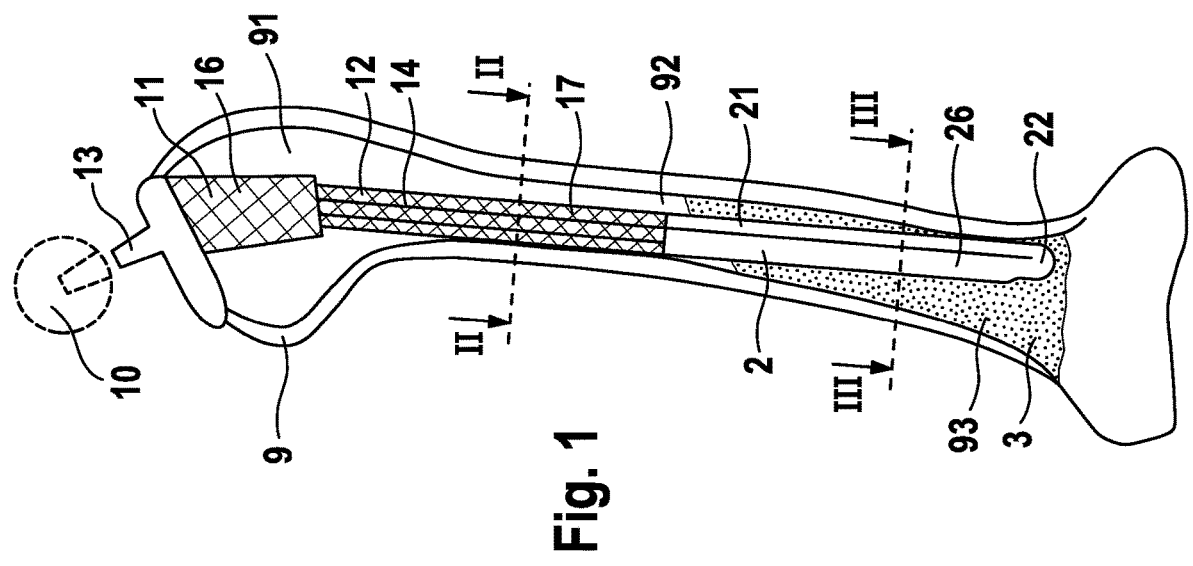
FIG. 1 shows a view of a revision prosthesis shaft in the projection on the LM plane.

The neck part 11 is inserted from above into the epimetaphysis 91 of the femur 9. At its upper end, the neck part has a retaining cone 13 pointing obliquely upward. A spherical joint head 10 is arranged on this retaining cone 13 and for this purpose has a conical bore for fitting it onto the retaining cone 13. The neck part 11 widens in its extent between its medial border (shown in the left in FIG. 1) and its lateral border (shown on the right in FIG. 1). The neck part 11 is shaped such that it substantially fills the epimetaphysis 91 of the femur 9 and, with its lateral walls, bears on the inner face of the bone wall in a load-bearing manner.

Figure 2:
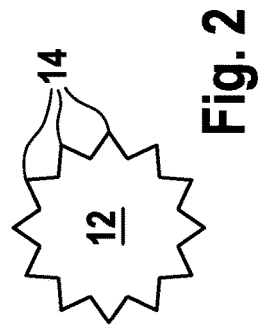
FIG. 2 shows a cross-sectional view of a shaft part of the revision prosthesis shaft.

The shaft part 12 is arranged on the end of the neck part 11 remote from the joint head 10. It adjoins the neck part 11 with smooth transitions. The shaft part 12 is of a generally elongate configuration and is substantially rod-shaped. In its middle and lower region, the shaft part 12 has a substantially round cross section with a plurality of longitudinal ribs 14, as shown in FIG. 2. The cross section is dimensioned such that it fills a medullary canal in the diaphysis 92 of the femur 9.

The revision shaft 1 is made of a biocompatible material. In the embodiment shown, cobalt-chromium-molybdenum (CoCrMo) is used as the material. The neck part 11 and the shaft part 12 are provided with a coating 16, 17 which promotes the incorporation of bone substance (this can be titanium, for example, or a coating with titanium or hydroxyapatite). In this way, through the incorporation of bone substance, it is possible to obtain a cementless but still secure anchoring of the revision shaft 1.

An extension 2 is arranged at the lower, far end of the shaft part 12. The extension 2 is likewise of a rod-like configuration. It is solid and produced as a single piece from one material. The material is preferably likewise cobalt-chromium-molybdenum (CoCrMo). The extension 2 is configured such that its surface 26 is designed for cemented implantation. The upper end 21 of the extension 2 is moreover configured such that it continues the outer contour of the lower end of the shaft part 12 without offset. The lower end of the extension 2 has an atraumatic shape with a rounded tip 22. The tip 22 has a smaller cross section than the upper end 21, such that the extension 2 tapers downwardly in the region of its tip 22.

Figure 3:
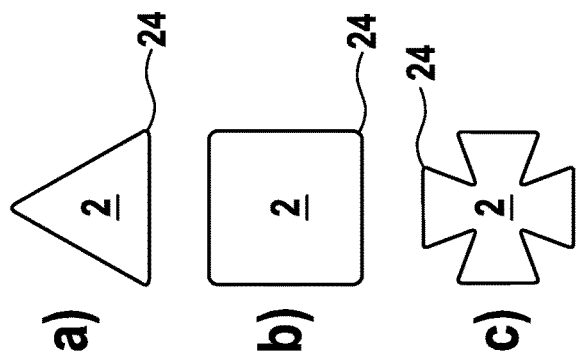

The extension 2 preferably does not have a round shape, but rather a non-round cross section. In this way, the extension 2 can contribute to securing against rotation. Whereas the cross section in the upper region of the extension is still adapted to that of the lower end of the shaft part 12, it changes in the downward direction and has a clearly non-round shape in the middle and lower region, for example a triangular shape or the shape of a clover leaf. Examples of such cross sections are shown in FIG. 3. In order to avoid trauma, the corners forming ribs 24 are preferably rounded here, so that there is no danger of them forming cuts or notches.

A cement bed 3 is provided for fixing the extension 2. It is arranged in the distal epimetaphysis 93 and reaches into the diaphysis 92. The cement bed 3 encases the extension 2 and thus fastens the latter along a distance extending far beyond the diaphysis 92 and deep into the distal epimetaphysis 93. The extension 2 is thus fastened in a reliable and stable manner not only in the narrow cross section of the medullary canal in the diaphysis 92 but also, by virtue of the cement bed 3, in the relatively wide cross section of the distal epimetaphysis 93. The overall distance along which the extension is fastened is thereby considerably increased according to the invention, which leads to the improved quality of fastening.

In combination with the cement bed 3, the non-round shape of the cross section (see FIG. 3) in the middle and lower region of the extension 2 additionally provides effective securing against undesired rotation.

FIG. 4 shows an enlarged detail of a transition with a coupling 4 between the shaft part 12 and the extension 2. The coupling 4 is designed as a cone connection with an outer cone 42 arranged at the upper end of the extension 2, which outer cone 42 engages in an inner cone 41 of complementary shape at the lower end of the shaft part 12 (it will be noted that the arrangement of outer cone and inner cone can also be reversed). This cone connection permits a secure and force-fit coupling of the extension 2 to the shaft part 12 of the revision shaft 1. Here, on account of the clamping action of the cone connection, a rotationally fixed connection between extension 2 and shaft part 12 is moreover obtained in the inserted state. The coupling 4 here defines the transition between shaft part 12 and extension 2. In the case of a one-piece design without coupling, the transition is defined from the surface configuration for cementless implantation at the shaft part 12 to the cemented implantation at the extension 2.

With this coupling 4 created by the cone connection, the extension 2 can already be pre-assembled such that it is inserted, together with the shaft part 12, from above into the femur 9. Alternatively, however, provision can also be made that the extension 2 is fitted independently of the shaft part 12. In this case, it can be fitted independently from above or, as may be preferable in some cases, also from the other side, i.e. from below. The latter option has the advantage that the extension 2 can be inserted directly into the distal epimetaphysis 93, without first being pushed through the diaphysis 92. This permits the use of extensions having large dimensions. Their width is no longer limited by the relatively narrow cross section of the passage in the diaphysis 92. This can optionally be exploited in order to use an extension 2 that has a larger diameter than the actual shaft part 12, in order thereby to obtain even more stability.

As has already been mentioned, the extension 2 is fastened substantially by the cement bed 3. This applies in particular for the region of the distal epimetaphysis 93. In order to ensure a stable initial positioning at the desired location, a centering star 5 can be provided. The latter is designed to be pushed onto the lower, free end with the tip 22 of the extension 2. The centering star 4 is mounted with its inside on the extension 2 and, by way of several bearing points 50 distributed about the periphery, bears with its outside on the bone wall of the femur 9 in the region of the distal epimetaphysis 93. The use of the centering star 5 is particularly advantageous when the extension 2 is first inserted from below directly into the distal epimetaphysis 93. However, its use is not limited to this case.

Alternatively, the revision prosthesis shaft can be designed as a kinked shaft 1'. It has a kink site 6, such that the extension 2 is not coaxial with the shaft part 12 but instead has a kink angle 60 relative to the latter. In the illustrative embodiment shown, the kink angle is intended to be 3° (shown larger than this in FIG. 5 for the sake of clarity). In the illustrative embodiment shown, the shaft 1 is configured in one piece with the extension 2. It will be noted that this may also be provided in the straight, unkinked variant.

The invention can be configured as a prosthesis system. In the latter, different neck parts 11, 11', 11" can be joined to the same or a different shaft part 12 in order to permit adaptation to different anatomical conditions.

The method for inserting the revision shaft 1 according to the invention is described with reference to two different examples shown in FIGS. 8 and 9. FIG. 8 shows the case where the revision shaft is inserted from above as one unit (either in one piece or with the extension 2 already inserted in the shaft part 12) through the epimetaphysis 91. Here, the extension 2 is pushed through the diaphysis 92 until its lower region with the tip 22 has reached the distal epimetaphysis 93. In this case, a cement bed 3 has preferably already been created in the distal epimetaphysis 93 before the insertion. This can be done, for example, by means of a cement syringe (not shown). Then, as the revision prosthesis shaft 1 with the attached extension 2 is pushed in, anchoring of the extension 2 takes place directly in the cement bed 3. In this way, the revision prosthesis shaft 1 is securely mounted, specifically also in the wide cross section of the distal epimetaphysis 93.

Alternatively, however, provision can also be made that the extension 2 is inserted independently, preferably from the opposite side. This is shown in FIG. 9. For this purpose, the extension 2 is pushed from below directly into the distal epimetaphysis 93, specifically to such an extent that the extension 2 is pushed with its upper end, and with the connection part (inner cone 42) arranged thereon, into the diaphysis 92. The middle and lower region, with the tip 22 of the extension, is then fastened by means of the cement bed 3 in the distal epimetaphysis 93. In a particularly expedient manner, said centering star 5 can be used here to ensure correct positioning of the extension 2 in the distal epimetaphysis 93. In a next step, the neck part is inserted with the shaft part 12 from above through the epimetaphysis 91, wherein the shaft part 12 is advanced into the diaphysis 92 and, with its complementary outer cone 41, is connected there to the inner cone 42 on the extension 2.

The latter method is particularly expedient when neck parts 11 of different sizes are intended to be used. Here, independently of the implantation of the extension 2, the appropriate size can be chosen according to the anatomical requirements. Examples of different sizes of neck parts 11, 11', 11" of a modular prosthesis set are shown in FIG. 7. They are fitted onto the shaft part 12 and thus form one unit that is jointly inserted, wherein a secure connection to the extension 2 is ensured by means of the coupling 4.

The invention claimed is:

1. A revision prosthesis shaft of a revision joint endoprosthesis for anchoring in an epimetaphyseal region of an elongate bone which comprises an epimetaphysis, a diaphysis and a distal epimetaphysis wherein the revision prosthesis shaft has, at the upper end, a neck part for receiving a joint piece and, adjoining the neck part, a shaft part whose surface is designed for adhesive agent-free fastening in the epimetaphysis and diaphysis and whose length is dimensioned such that it reaches into the diaphysis of the bone, wherein a distal epimetaphyseal extension for the shaft is provided at the far end of the shaft part, the length of which extension is dimensioned such that its tip reaches into the distal epimetaphysis of the bone, wherein the extension is designed for fastening in the distal epimetaphysis with an adhesive agent.

2. The revision prosthesis shaft as claimed in claim 1, wherein the extension is configured as a single piece.

3. The revision prosthesis shaft as claimed in claim 1, wherein a transition between shaft part and extension is in the region of 40-60% of the total length of the shaft.

4. The revision prosthesis shaft as claimed in claim 3, wherein a kink site lies in the region of the transition, but offset in relation to the transition.

5. The revision prosthesis shaft as claimed in 1, wherein the shaft part forms, with the extension, a kinked shaft with a kink angle of 1° to 5°.

6. The revision prosthesis shaft as claimed in claim 1, wherein the extension has a tapering configuration in the region of its tip.

7. The revision prosthesis shaft as claimed in claim 1, wherein the extension is substantially straight in its distal region.

8. The revision prosthesis shaft as claimed in claim 1, wherein the extension has a non-round cross section which is shaped to inhibit rotation in each case with rounded corners.

9. The revision prosthesis shaft as claimed in claim 1, wherein the extension is of such a length that the total length of the shaft is at least 22 times the diameter.

10. The revision prosthesis shaft as claimed claim 1, wherein the shaft part is configured in one piece with the extension.

11. The revision prosthesis shaft as claimed in claim 1, wherein the extension is configured separately, and a coupling site is provided for rotationally fixed connection of the extension to the shaft part.

12. The revision prosthesis shaft as claimed in claim 1, wherein a centering element is provided on the extension.

13. The revision prosthesis shaft as claimed in claim 1, wherein the extension has an elastic modulus of 100 to 250 GPa.

14. The revision prosthesis shaft as claimed in claim 1, wherein the shaft is of a modular configuration with an exchangeable neck part.

15. A method for implanting a revision prosthesis shaft of a revision joint endoprosthesis for anchoring in an epimetaphyseal region of an elongate bone with an epimetaphysis, a diaphysis and a distal epimetaphysis, wherein the revision prosthesis shaft has, at the upper end, a neck part for receiving a joint piece and, adjoining the neck part, a shaft part whose surface is designed for adhesive agent-free fastening in the epimetaphysis and whose length is dimensioned such that it reaches into the diaphysis of the bone, and a distal epimetaphyseal extension is provided at the far end of the shaft part, the length of which extension is dimensioned such that its tip reaches into the distal epimetaphysis of the bone, wherein the extension is designed for cemented fastening in the distal epimetaphysis, said method comprising the steps of:

inserting the shaft part with the neck part from the proximal direction into the epimetaphyseal region of the elongate bone, creating a receiving bed of adhesive material in the distal epimetaphysis, inserting the extension into the distal epimetaphysis, wherein the extension forms a continuation of the shaft part beyond the diaphysis into the distal epimetaphysis.

16. The method as claimed in claim 15, further comprising use of a revision prosthesis shaft as claimed in claim 2.

17. The revision prosthesis shaft as claimed in claim 8, wherein the cross section varies along the shaft and the extension, wherein the cross section changes from a round cross section to the non-round cross-section of the extension.

\* \* \* \* \*